United States Patent [19]
Hoff et al.

[11] 3,942,531
[45] Mar. 9, 1976

[54] APPARATUS FOR BREAKING-UP, WITHOUT CONTACT, CONCREMENTS PRESENT IN THE BODY OF A LIVING BEING

[75] Inventors: Günter Hoff, Meersburg; Armin Behrendt, Friedrichshafen, both of Germany

[73] Assignee: Dornier System GmbH, Germany

[22] Filed: Sept. 11, 1974

[21] Appl. No.: 505,093

[30] Foreign Application Priority Data
Oct. 12, 1973  Germany............................ 2351247

[52] U.S. Cl.............. 128/328; 340/8 FT; 340/12 SD
[51] Int. Cl.².................... A61B 17/00; A61N 3/00
[58] Field of Search......... 128/328, 24 A; 340/8 FT, 340/12 SD

[56] References Cited
UNITED STATES PATENTS

| | | | |
|---|---|---|---|
| 2,668,529 | 2/1954 | Huter | 128/24 A |
| 3,237,623 | 3/1966 | Gordon | 128/24 A |
| 3,251,219 | 5/1966 | Hertz et al. | 128/24 A |
| 3,269,173 | 8/1966 | von Ardenne | 128/24 A |
| 3,283,294 | 11/1966 | Schrom | 340/8 FT |
| 3,347,336 | 10/1967 | Nash, Jr. | 340/12 SD |
| 3,356,086 | 12/1967 | Behney | 128/24 A |
| 3,387,604 | 6/1968 | Erikson | 128/24 A |
| 3,537,542 | 11/1970 | Dubois et al. | 240/12 SD |
| 3,735,764 | 5/1973 | Balaev et al. | 128/328 |

FOREIGN PATENTS OR APPLICATIONS

| | | | |
|---|---|---|---|
| 1,045,012 | 6/1951 | France | 128/24 A |

*Primary Examiner*—Channing L. Pace
*Attorney, Agent, or Firm*—James E. Bryan

[57] ABSTRACT

This invention relates to an apparatus for breaking-up, without contact, concrements present in the body of a living being, which comprises waveguide means filled with a liquid medium and adapted to be placed against said body, and means for generating shock waves within said waveguide means.

3 Claims, 3 Drawing Figures

APPARATUS FOR BREAKING-UP, WITHOUT CONTACT, CONCREMENTS PRESENT IN THE BODY OF A LIVING BEING

The present invention relates to an apparatus for breaking-up, without contact, concrements present in the body of a living being, by means of a shock wave exciter and a waveguide resting against the body and being constructed as a coupling device.

Known in the art is an instrument designed to be inserted into natural body orifices and for seizing and pulling out extraneous objects present therein (DAS No. 1,283,434), wherein by means of flexible wires a trapping or catching cage is formed with serves, for example, for removing gallstones.

Further known in the art is an instrument for breaking-up kidney stones (DAS No. 1,259,503). In this case, a milling head is introduced into the body of the patient. A milling needle head, adapted to be driven, effects the mechanical destruction of the kidney stone. During the breaking-up of the kidney stone, or the removal thereof, the known devices must contact the kidney stones so that the introduction of instruments into the human body is inevitable. This means a long and difficult operation; in addition, the orifices of the body may be damaged so that surgery becomes necessary.

It is the object of the present invention to provide an apparatus for breaking-up, without contact, concrements present in the human body by means of shock waves.

This object is obtained, in accordance with the present invention, by virtue of the fact that the shock waves are generated by means of a spark discharge in a liquid medium within a waveguide constructed as a coupling member. Instead of the spark discharge, an explosive charge also may be employed. This produces significant advantages. The destruction of kidney stones is possible without any surgery and without the introduction of sondes.

The kidney stone is located with respect to its size and its position in the body of the patient, for example by means of an X-ray picture. Thereafter, the stone is acted upon by means of shock waves adapted to be dosed or quantitatively regulated and focused so that it will disintegrate to a fine grit which is easily flushed out of the body in a natural manner.

The present invention is based upon the knowledge that shock waves will cause a spalling or destructive effect on material having a low tensile strength whenever there is a transition from a medium having a high sound wave resistance to a medium having a low sound wave resistance. It now has been found that the sound wave resistance of human and animal tissue corresponds approximately to the sound wave resistance of water. It is for this reason that, used as coupling member between the body and the shock wave exciter, is a coupling member in the form of a waveguide filled with a liquid medium (for example water). If care is taken to ensure that the shock waves are directed toward the concrement, other parts of the body are not affected thereby. Experiments have shown that bones in the human body are not damaged by this procedure because of their high tensile strength and the brevity of the pulse.

According to a further advantageous embodiment of the present invention, the waveguide has a circular cross-section and the walls thereof are elliptical in longitudinal cross-section. In this case, the starting point of the shock wave is positioned in one focal point of the ellipse, and the concrement to be destroyed is positioned in another focal point of the ellipse. This apparatus ensures that a high energy density is present only in the zone of the concrement.

The destruction of concrements substantially depends upon the rate of the pressure rise. The size of the parts chipping off, on the other hand, is determined by the duration of the shock wave pulse. In order to destroy a large concrement, it may be advantageous to employ a first pulse of a longer duration in order to break the concrement into larger pieces. Subsequently, the comminution into fragments may be carried out with very brief pulses, which fragments may be flushed out in a natural fashion through the ureter. In order to obtain fragments having approximately millimeter size, shock wave durations of about $10^{-6}$ seconds are necessary. About 5 to 10 shock waves are required for the complete destruction of a kidney stone, having a diameter of approximately 1 centimeter, into fragments that can be passed.

Further advantages, features and possibilities of application of the present invention will become apparent from the accompanying drawings, wherein.

Figure 1:
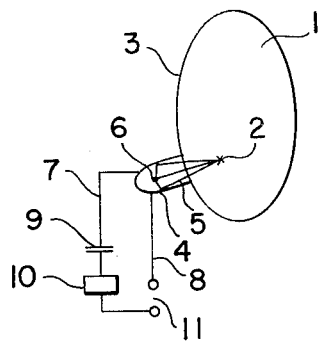
FIG. 1 is an illustration, in principle, in a top plan view, of an apparatus designed for breaking-up, without contact, concrements present in the body of a living being.

FIG. 1 shows in a top plan view a human body 1 in which a concrement 2 is present. The concrement 2 may be a gallstone, a bladder stone, or a kidney stone. Placed upon the skin 3 of the body 1 is a coupling device or waveguide 4. Present on the inside 5 of the coupling device 4 is a medium which in its density, and therewith also in its sound wave resistance, corresponds to the density of the human body. It has been found that water may be used therefor. Further present on the inside 5 is a shock wave generator or exciter 6 which is shown more precisely in FIGS. 2 and 3. From the shock wave exciter or generator 6 lines 7 and 8 extend to a capacitor 9 and to a control device 10. A current source is provided at 11.

Figure 2:
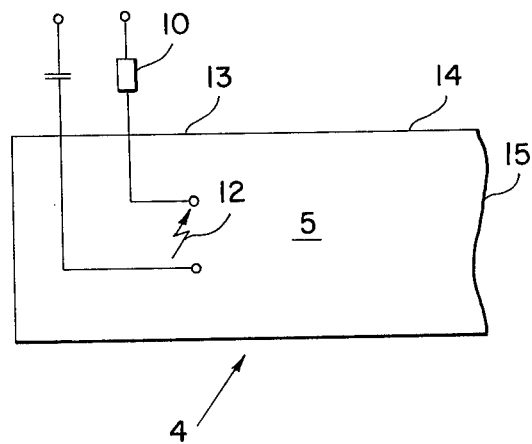
FIG. 2 illustrates an apparatus for generating shock waves by means of spark discharge, which is accommodated in a waveguide.

It is apparent from FIG. 2 that the shock wave exciter or generator 6 is a spark discharge path 12 which is here mounted in a cylindrical pipe 13. Positioned at the end 14 of the pipe 13 is a diaphragm 15 which is adapted to be placed or mounted — preferably without an air gap — upon the surface 3 of the body 1. By actuating the control unit 10, shock waves are transmitted from the spark discharge path 12 via the interior 5 of the coupling device 4, being filled with water, onto the diaphragm 15, and from there to the concrement 2 present in the body 1. By means of the control unit 10, the pulse duration and the pulse intensity of the shock wave exciter or generator 6 may be varied. Experiments carried out with a voltage of 10 kV at 70 Hz resulted in the destruction of the kidney stones to grit.

Figure 3:
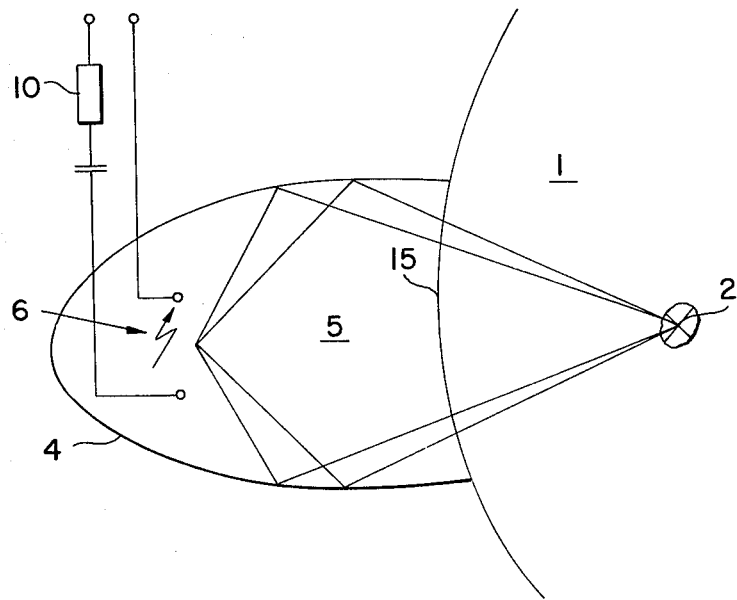
FIG. 3 is a representation, in principle, of a focusing device for concentrating the shock waves in the area of the concrement, also in a top plan view.

The same reference numerals employed in FIGS. 1 and 2 have been used also in FIG. 3. In this case, the coupling device or the waveguide 4 has an elliptical configuration in a side view thereof so that the shock waves emanating from the shock wave source 6 are reflected at the edges and are concentrated in the second focal point of the ellipse in which the concrement 2 is present. The wall of the waveguide 4 consists, for example, of a metal; its interior 5 is filled with water. The treating physician has at his disposal several elliptical coupling devices 4 of varying dimensions so that the anatomical requirements can be duly taken into account.

Acting in the same manner as the spark discharge path 12, the shock wave exciter or generator 6 also may be an explosive charge.

It will be obvious to those skilled in the art that many modifications may be made within the scope of the present invention without departing from the spirit thereof, and the invention includes all such modifications.

What is claimed is:

1. An apparatus for breaking-up, without contact, a concrement present in the body of a living being, which comprises waveguide means having a circular cross-section and elliptical walls in longitudinal cross-section,
   diaphragm means on an end face of said waveguide means and adapted to be placed against said body,
   liquid means filling said waveguide means,
   and spark discharge means in said waveguide means and located at one focus of the ellipse formed by said elliptical walls,
   whereby shock waves generated by said spark discharge means are reflected and focused by the walls of said waveguide means, pass through said liquid, said diaphragm means, and tissue of said body, and are adapted to impinge upon and break-up a concrement located at the other focal point of the ellipse formed by said elliptical walls.

2. An apparatus according to claim 1 in which said diaphragm means is adapted to be placed on said body in an air-tight manner.

3. An apparatus according to claim 1 in which said liquid is water.

* * * * *